(12) United States Patent
Parthasaradhi Reddy et al.

(10) Patent No.: US 8,420,822 B2
(45) Date of Patent: Apr. 16, 2013

(54) OPTICAL RESOLUTION OF SUBSTITUTED 2-(2-PYRIDINYLMETHYLSULPHINYL)-1H-BENZIMIDAZOLES

(75) Inventors: Bandi Parthasaradhi Reddy, Andhrapradesh (IN); Kura Rathnakar Reddy, Andhrapradesh (IN); Rapolu Raji Reddy, Andhrapradesh (IN); Dasari Muralidhara Reddy, Andhrapradesh (IN); Bandi Vamsi Krishna, Andhrapradesh (IN); Ayyalasomayajula Satya Srinivas, Andhrapradesh (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 12/665,195

(22) PCT Filed: Oct. 9, 2009

(86) PCT No.: PCT/IN2009/000567
§ 371 (c)(1),
(2), (4) Date: Dec. 17, 2009

(87) PCT Pub. No.: WO2011/042910
PCT Pub. Date: Apr. 14, 2011

(65) Prior Publication Data
US 2012/0197021 A1 Aug. 2, 2012

(51) Int. Cl.
*C07D 401/00* (2006.01)
*A61K 31/44* (2006.01)
(52) U.S. Cl.
USPC ...................................... 546/273.7

(58) Field of Classification Search ........................ None
See application file for complete search history.

(56) References Cited

U.S. PATENT DOCUMENTS
2006/0217423 A1    9/2006  Deng et al.

FOREIGN PATENT DOCUMENTS
WO    2008092939 A2    8/2008
WO    2009061529 A1    5/2009

OTHER PUBLICATIONS
International Search Report and Written Opinion for PCT/IN2009/000567, dated May 16, 2011.
Claims of PCT/IN2009/000567, filed Oct. 9, 2009.

*Primary Examiner* — Janet Andres
*Assistant Examiner* — Heidi Reese
(74) *Attorney, Agent, or Firm* — Caesar, Rivise, Bernstein, Cohen & Pokotilow, Ltd.

(57) ABSTRACT

The present invention relates to process for preparation of optical resolution of substituted 2-(2-pyridinylmethylsulphinyl)-1H-benzimidazoles either as a single enantiomer or in an enantiomerically enriched form. Thus, for example, R-1,1'-binaphtyl-2-2'-diyl hydrogen phosphate was reacted with 2-[[[3-methyl-4-(2,2,2-trifluoro-ethoxy)-2-pyridinyl]methyl]sulfinyl]-1H-benzimidazole (Lansoprazole) in a mixture of benzene and cyclohexane to obtain diasteremeric complexes. The diasteremeric complexes were subjected to fractional crystallization to obtain R-2-[[[3-methyl-4-(2,2,2-trifluoro-ethoxy)-2-pyridinyl]methyl]sulfinyl]-1H-benzimidazole.R-1,1'-binaphthyl-2-2'-diyl hydrogen phosphate. The separated isomer was treated with sodium bicarbonate in a mixture of ethyl acetate and water to obtain R-2-[[[3-methyl-4-(2,2,2-trifluoro-ethoxy)-2-pyridinyl]methyl]sulfinyl]-1H-benzimidazole (dexlansoprazole).

20 Claims, No Drawings

OPTICAL RESOLUTION OF SUBSTITUTED 2-(2-PYRIDINYLMETHYLSULPHINYL)-1H-BENZIMIDAZOLES

FIELD OF THE INVENTION

The present invention relates to process for preparation of optical resolution of substituted 2-(2-pyridinylmethylsulphinyl)-1H-benzimidazoles either as a single enantiomer or in an enantiomerically enriched form.

BACKGROUND OF THE INVENTION

Substituted 2-(2-pyridinylmethylsulfinyl)-1H-benzimidazoles such as for example lansoprazole, omeprazole, pantoprazole and rabeprazole including their stereoisomers are inhibitors of gastric acid secretion. Some compounds useful as prodrugs of proton pump inhibitors are disclosed in U.S. Pat. No. 6,559,167.

These compounds and structurally related compounds have a stereogenic center at sulfur and therefore exist as two optical isomers. The resolution processes of racemates of these compounds were, for example, disclosed in DE 4035455 and WO 94/27988. According to these processes chiral ether such as fenchyloxymethyl or chiral acyloxy methyl group such as mandeloyl—is introduced into the 1-position of benzimidazole ring of racemic sulfoxide compound to obtain a diastereomeric mixture, diastereomers are then separated and desired isomer is liberated from a separated diastereomer. The process requires either the preparation of fenchyloxymethyl chloride and then reaction with the racemic compound; or introduction of chloromethyl group on 1-position of benzimidazole ring, followed by reaction with the chiral auxiliary. We found that these intermediates are difficult to prepare and involve in many steps.

U.S. Pat. No. 7,176,319 B2 disclosed a resolution of racemic sulfoxide compounds using chiral camphoursulfonyl chloride.

U.S. Pat. Nos. 5,948,789 and 7,365,206 B2 disclosed stereoselective oxidation methods for the preparation of chiral substituted 2-(2-pyridinylmethylsulfinyl)-1H-benzimidazoles.

International Patent Publication No. WO 2008/004245 and CN 1087739 disclosed processes for preparation of an optically pure or optically enriched enantiomer of a sulphoxide compound using R- or S-1,1'-bi-2-naphthol (R- or S-BINOL).

Lansoprazole, chemically 2-[[[3-methyl-4-(2,2,2-trifluoro-ethoxy)-2-pyridinyl]methyl]sulfinyl]-1H-benzimidazole were disclosed in European Patent No. 0174726 and U.S. Pat. No. 4,628,098. Lansoprazole was a well-known gastric acid secretion inhibitor, and was useful for prophylaxis and therapy of digestive ulcers (e.g. gastric ulcer, duodenal ulcer) and gastritis. The generic name dexlansoprazole is marketed by Takeda Pharms under the brand KAPIDEX.

U.S. Pat. No. 6,462,058 disclosed a crystal of R-lansoprazole and its use as an anti-ulcer agent. U.S. Pat. Nos. 6,462,058 and 6,664,276 and International Patent Publication No. WO 00/78745 all described the synthesis of a crystal of R-lansoprazole. Exemplary methods for such synthesis include:

a) Optical resolution of substituted 2-(2-pyridinylmethylsulfinyl)-1H-benzimidazoles by a fractional crystallization method, which includes forming a salt between a racemate and an optically active compound (for example, (+)-mandelic acid, (−)-mandelic acid, (+)-tartaric acid, (−)-tartaric acid, camphoursulfonyl chloride, or camphanic acid). The diastereoisomeric salt is separated by fractional crystallization and then subjected to a neutralization process to give a free optical isomer.

b) The chiral column method includes a method in which a racemate or a salt is applied to a column for optical isomer separation. In liquid chromatography, for example, optical isomers are separated by adding the racemate to a chiral column (such as the Daicel® series (produced by Daicel Chemical Industries, Ltd.), and eluting in water, a buffer (for example, a phosphate), an organic solvent (for example, hexane, ethanol, methanol, isopropanol, acetonitrile, triethylamine, or mixtures thereof) or mixtures of the foregoing.

c) The asymmetric oxidation process includes subjecting substituted 2-(2-pyridinylmethylsulfinyl)-1H-benzimidazoles to an asymmetric oxidation to obtain enantiomer of substituted 2-(2-pyridinylmethylsulfinyl)-1H-benzimidazoles, followed by crystallizing the resultant isomer.

The optical resolutions of (R)-(+)-lansoprazole from racemic lansoprazole were disclosed in International Patent Application No. WO 2009/087672.

We have found that the use of various chiral acids such as chiral camphoursulfonyl chloride, camphanic acid, (+)-mandelic acid, (−)-mandelic acid, (+)-tartaric acid and (−)-tartaric acid for the resolution of substituted 2-(2-pyridinylmethylsulphinyl)-1H-benzimidazoles does not result in the separation of enantiomers.

We have discovered a novel process for optical resolution of substituted 2-(2-pyridinylmethylsulphinyl)-1H-benzimidazoles either as a single enantiomer or in an enantiomerically enriched form. The object of the present invention is to provide an improved and commercially viable process for optical resolution of substituted 2-(2-pyridinylmethylsulphinyl)-1H-benzimidazoles. The process of the invention can be applied to obtain an enantiomer of substituted 2-(2-pyridinylmethylsulphinyl)-1H-benzimidazoles with an optical purity to the extent of 100%.

SUMMARY OF THE INVENTION

In accordance with one aspect of the present invention, there is provided a novel process for resolution of substituted 2-(2-pyridinylmethylsulphinyl)-1H-benzimidazoles of formula (I) or a mixtures thereof;

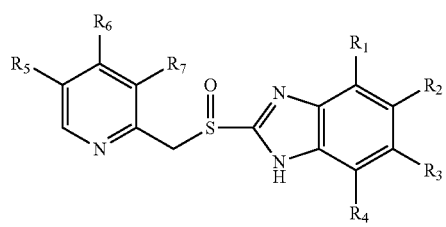

Wherein $R_1$-$R_4$ are the same or different and selected from hydrogen, alkyl, alkoxy, halogen, halo-alkoxy, alkylcarbonyl, alkoxycarbonyl, oxazolyl, trifluoroalkyl, or adjacent groups $R_1$-$R_4$ form ring structures which may be further substituted; and $R_5$, $R_6$ and $R_7$ are same or different and selected from hydrogen, alkyl, alkylthio, alkoxy optionally substituted by fluorine, alkoxyalkoxy, dialkylamino, piperidino, morpholino, halogen, phenylalkyl and phenylalkoxy;

which comprises:

a) reacting substituted 2-(2-pyridinylmethylsulphinyl)-1H-benzimidazoles of formula (I) or a mixtures thereof with a chiral 1,1'-binaphtyl-2-2'-diyl hydrogen phosphate (BNPPA) to obtain corresponding diastereomer complexes;

b) isolating preferentially one diastereomer complex from the mixture of diastereomer complexes; and c) converting the isolated diastereomer complex to the corresponding enantiomer of the compound of formula (I).

Yet another aspect of the present invention there is provided a novel compound selected from formulae II(i)-II(iv) or a mixture thereof:

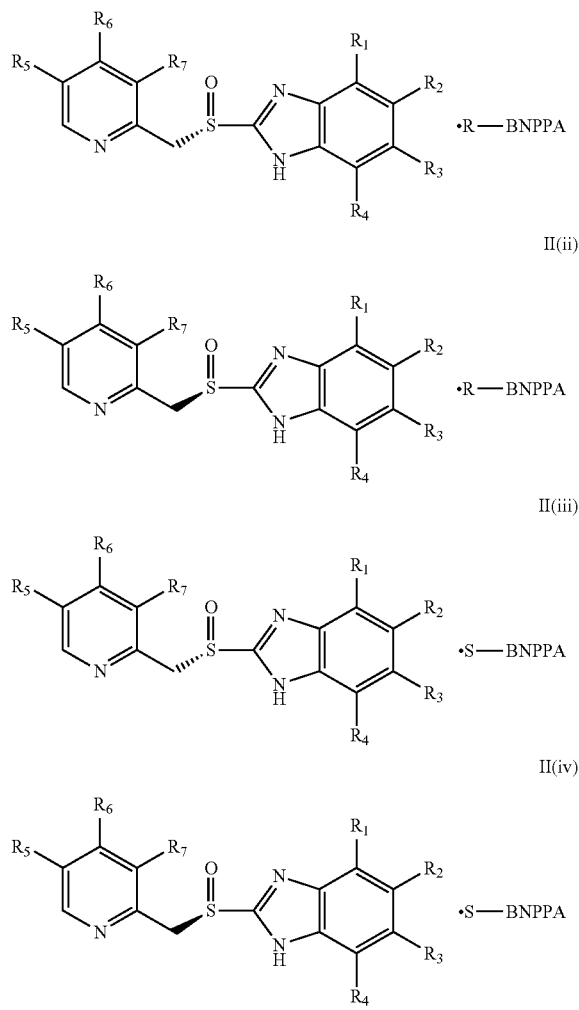

DETAILED DESCRIPTION OF THE INVENTION

According to one aspect of the present invention, there is provided a novel process for resolution of substituted 2-(2-pyridinylmethylsulphinyl)-1H-benzimidazoles of formula (I) or a mixtures thereof;

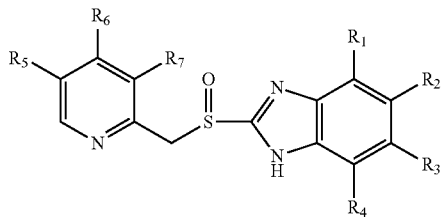

Wherein $R_1$-$R_4$ are the same or different and selected from hydrogen, alkyl, alkoxy, halogen, halo-alkoxy, alkylcarbonyl, alkoxycarbonyl, oxazolyl, trifluoroalkyl, or adjacent groups $R_1$-$R_4$ form ring structures which may be further substituted; and $R_5$, $R_6$ and $R_7$ are same or different and selected from hydrogen, alkyl, alkylthio, alkoxy optionally substituted by fluorine, alkoxyalkoxy, dialkylamino, piperidino, morpholino, halogen, phenylalkyl and phenylalkoxy;

which comprises:

a) reacting substituted 2-(2-pyridinylmethylsulphinyl)-1H-benzimidazoles of formula (I) or a mixtures thereof with a chiral 1,1'-binaphtyl-2-2'-diyl hydrogen phosphate (BNPPA) to obtain corresponding diastereomer complexes;

b) isolating preferentially one diastereomer complex from the mixture of diastereomer complexes; and c) converting the isolated diastereomer complex to the corresponding enantiomer of the compound of formula (I).

Without bound to the nature of interaction (such as salt, complex etc.) between 2-(2-pyridinylmethylsulphinyl)-1H-benzimidazoles of formula (I) and chiral 1,1'-binaphtyl-2-2'-diyl hydrogen phosphate, the compounds of 2-(2-pyridinylmethylsulphinyl)-1H-benzimidazoles of formula (I) with 1,1'-binaphtyl-2-2'-diyl hydrogen phosphate are referred to, for example, as 2-(2-pyridinylmethylsulphinyl)-1H-benzimidazoles of formula (I). 1,1'-binaphtyl-2-2'-diyl hydrogen phosphate compounds. The reaction of 2-(2-pyridinylmethylsulphinyl)-1H-benzimidazoles of formula (I) or a mixtures thereof with R-BNPPA or S-BNPPA in step (a) may preferably be carried out in a solvent or a mixture thereof and adding a base. There is no restriction on the use of a particular base, but preferably, inorganic bases such as alkaline metal hydroxides, carbonates or bicarbonates, or ammonia; or organic bases such as trimethylamine or triethylamine may be used. Any suitable solvent such as alcohols such as methanol, ethanol or isopropyl alcohol; alkyl benzene such as toluene or xylene; cyclohexane, hexane, ethyl acetate, benzene solvent may be used. Preferably, the solvent is a mixture of benzene or ethylacetate or toluene and cyclohexane or hexane. More preferably, the solvent is a mixture of benzene and cyclohexane. The diastereomer complexes obtained in the step (a) may remain in the solution to proceed for further operations or may be isolated as a crystalline product or as a residual mass to proceed to the further operations. More than or less than one mole equivalent of chiral BNPPA with respect to the racemic substituted 2-(2-pyridinylmethylsulphinyl)-1H-benzimidazoles of formula (I) may be used.

The diastereomer complexes formed above are then separated. It is well known that diastereomer complexes differ in their properties such as solubility and they can be separated based on the differences in their properties. The separation of the diastereomer complexes can be performed using the methods known to the person skilled in the art. These methods include chromatographic techniques and fractional crystallization, preferable method being fractional crystallization.

The solution of the diastereomer complexes may be a solution of the reaction mixture obtained as above or a solution prepared by dissolving the isolated diastereomer complexes in a solvent. Any solvent may be used so long as it can be used for the separation. The preferable solvent is selected from alkyl benzene such as toluene and xylene; benzene; cyclohexane; esters such as ethyl acetate, methyl acetate, isopropyl acetate, tert-butyl methyl acetate and ethyl formate; alcohols such as methanol and ethanol; and a mixture thereof. The more preferable solvent is selected from a mixture of toluene, ethyl acetate, benzene and cyclohoeaxne.

Crystallization of preferentially one diastereomer complex from the solution of diastereomer complexes can be performed by conventional methods such as cooling, partial removal of solvents, seeding or a combination thereof. Fractional crystallization may also occur from the solution under condition of diasteromeric complex formation. Isolation can be repeated until the desired chiral purity is obtained. But, usually one or two isolations may be sufficient. The separated solid may be collected by the method known such as centrifugation or filtration.

The separated diastereomers is converted in step (c) to the corresponding enantiomer of 2-(2-pyridinylmethylsulphinyl)-1H-benzimidazoles of formula (I) preferably by suspending or dissolving the separated diasteromer in water or solvent; or a mixture thereof and adding a base. There is no restriction on the use of a particular base, but preferably, inorganic bases such as alkaline metal hydroxides, carbonates or bicarbonates, or ammonia; or organic bases such as trimethylamine or triethylamine may be used. Preferably, the conversion may be carried out in water, alcohols such as methanol, ethanol, isopropyl alcohol, ketones such as acetone, methyl ethyl ketone, methyl isopropyl ketone, methyl t-butyl ketone, acetonitril, ethyl acetate, isopropyl acetate, methyl acetate, N,N-dimethylformamide, tetrahydrofuran solvent may be used. More preferably, the solvent is selected from methanol, ethanol, isopropyl alcohol and ethyl acetate, and still more preferably, the solvent is a mixture of water and ethyl acetate.

The invention is not restricted to perfectly racemic compound and can also be applied to optical separation of enantiomeric mixture enantiomerically enriched with one enantiomer. Thus, the invention also serves as optical purification of substituted 2-(2-pyridinylmethylsulphinyl)-1H-benzimidazoles of formula (I) isomers.

The resolution of substituted 2-(2-pyridinylmethylsulphinyl)-1H-benzimidazoles of formula (I) to obtain enantiomer of substituted (2-(2-pyridinylmethylsulphinyl)-1H-benzimidazoles of formula (I) may be represented by the following scheme 1:

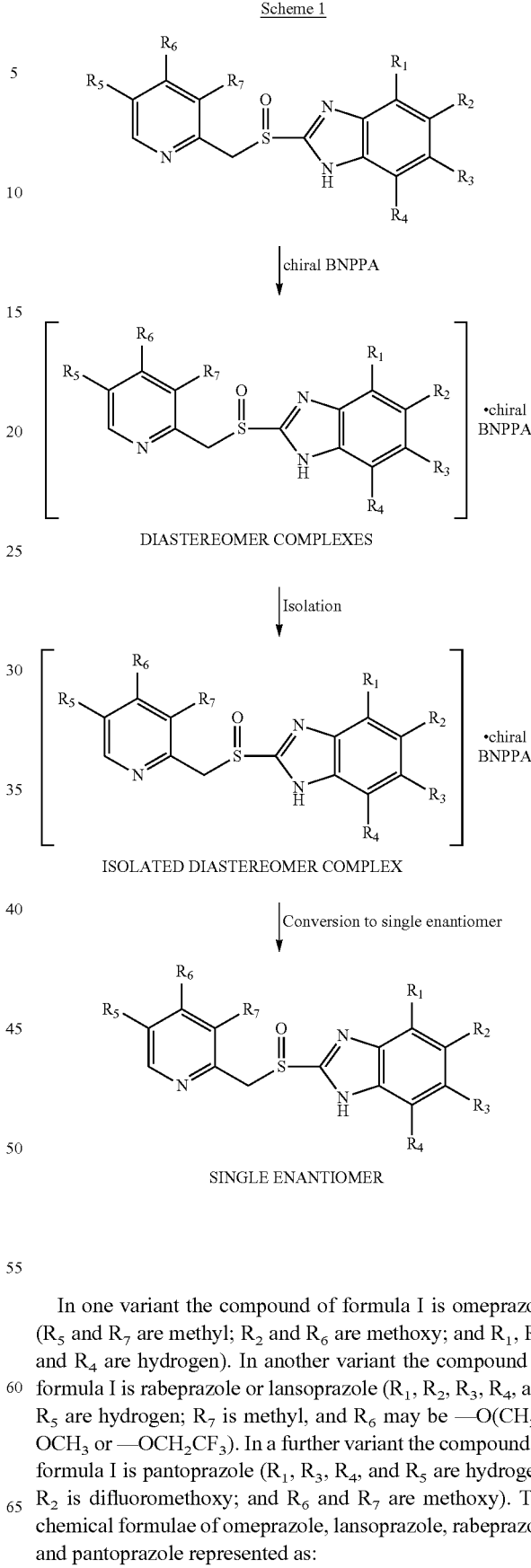

In one variant the compound of formula I is omeprazole ($R_5$ and $R_7$ are methyl; $R_2$ and $R_6$ are methoxy; and $R_1$, $R_3$, and $R_4$ are hydrogen). In another variant the compound of formula I is rabeprazole or lansoprazole ($R_1$, $R_2$, $R_3$, $R_4$, and $R_5$ are hydrogen; $R_7$ is methyl, and $R_6$ may be —O(CH$_2$)$_3$OCH$_3$ or —OCH$_2$CF$_3$). In a further variant the compound of formula I is pantoprazole ($R_1$, $R_3$, $R_4$, and $R_5$ are hydrogen; $R_2$ is difluoromethoxy; and $R_6$ and $R_7$ are methoxy). The chemical formulae of omeprazole, lansoprazole, rabeprazole and pantoprazole represented as:

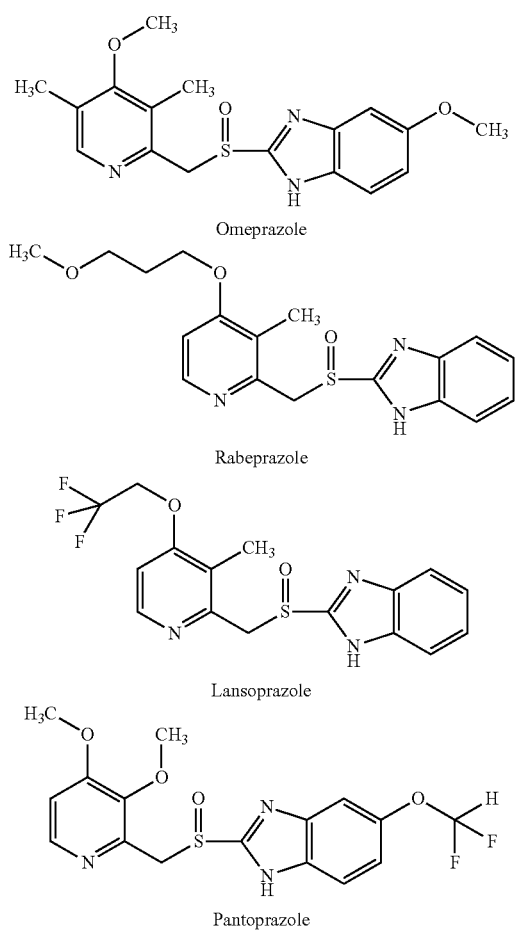

Omeprazole

Rabeprazole

Lansoprazole

Pantoprazole

The chemical formulae of (R)-BNPPA and (S)-BNPPA represented as:

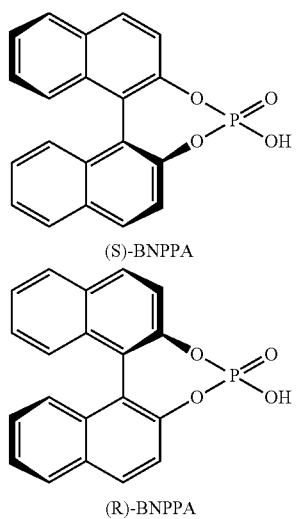

(S)-BNPPA (R)-BNPPA

As a preferred process of the invention, the resolution of racemic 2-[[[3-Methyl-4-(2,2,2-trifluoro-ethoxy)-2-pyridinyl]methyl]sulfinyl]-1H-benzimidazole (Lansoprazole) may be carried out by the process which comprises:

a) reacting substituted racemic 2-[[[3-Methyl-4-(2,2,2-trifluoro-ethoxy)-2-pyridinyl]methyl]sulfinyl]-1H-benzimidazole (Lansoprazole) with R-1,1'-binaphtyl-2-2'-diyl hydrogen phosphate (R-BNPPA) in the mixture of benzene or toluene and cyclohexane in the presence of a base to obtain corresponding diastereomer complexes;

b) isolating preferentially one diastereomer complex from the mixture of diastereomer complexes; and c) converting the isolated diastereomer complex to the corresponding (R)-2-[[[3-Methyl-4-(2,2,2-trifluoro-ethoxy)-2-pyridinyl]methyl]sulfinyl]-1H-benzimidazole (Dexlansoprazole) in a mixture of water and ethyl acetate in the presence of a base.

As a specific example of the resolution of racemic lansoprazole to obtain dexlansoprazole may be represented by the following scheme 2:

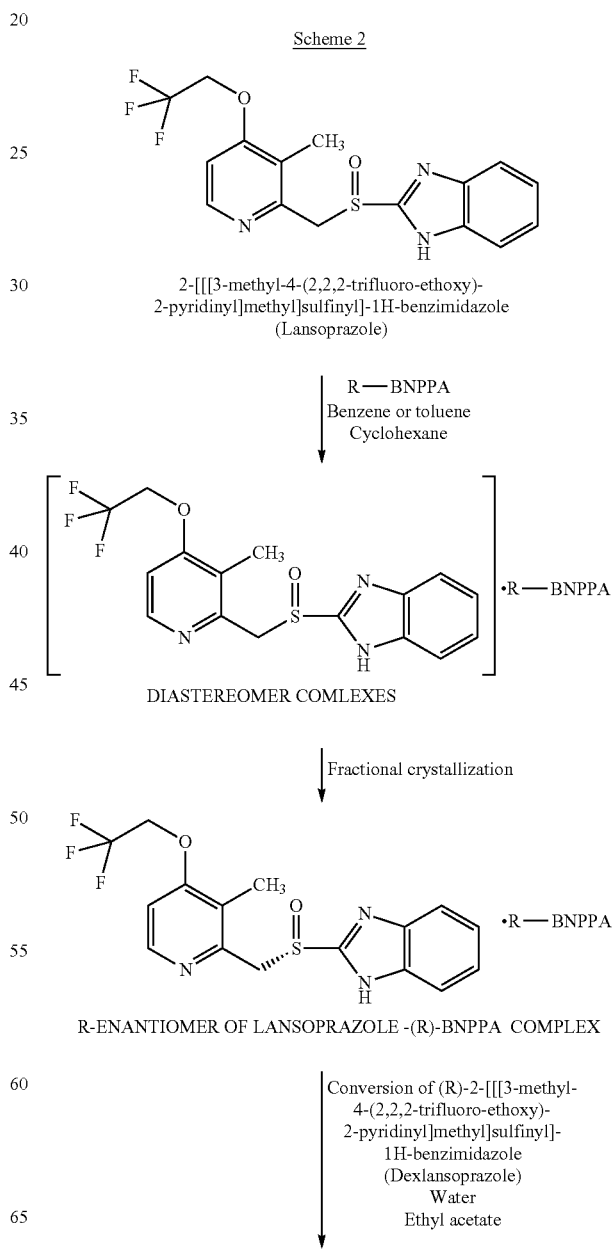

Scheme 2

-continued

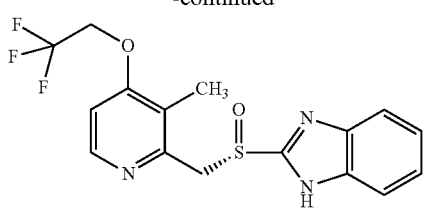

(R)-2-[[[3-methyl-4-(2,2,2-trifluoro-ethoxy)-2-pyridinyl]methyl]sulfinyl]-1H-benzimidazole
(Dexlansoprazole)

Similarly, S-BNPPA may be used instead of R-BNPPA to obtain S-enantiomer of lansoprazole.

According to another aspect of the present invention there is provided a novel compound selected from formulae II(i)-II(iv) or a mixture thereof:

II(i)

$$\text{structure}$$

·R-BNPPA

II(ii)

·R-BNPPA

II(iii)

·S-BNPPA

II(iv)

·S-BNPPA

Preferred compounds of formulae II(i)-II(iv) as shown below:

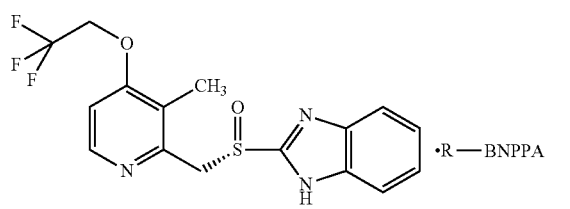

III(a)

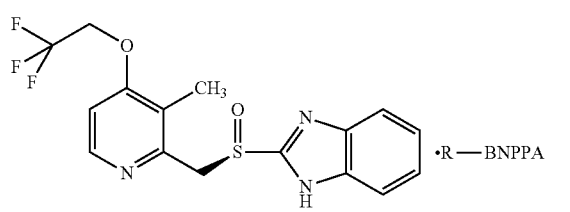

III(b)

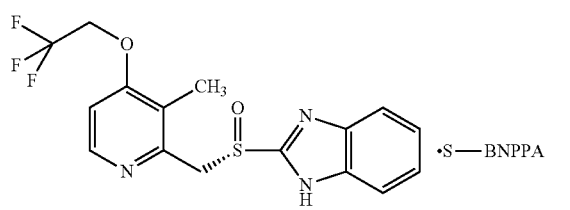

III(c)

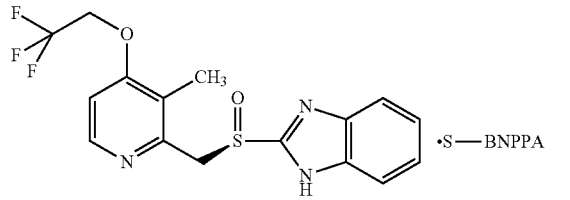

III(d)

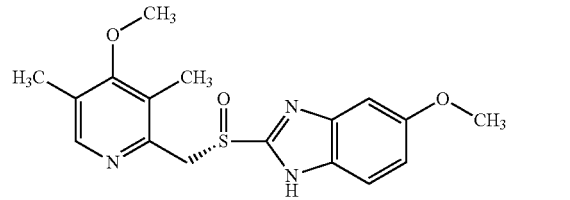

III(e)

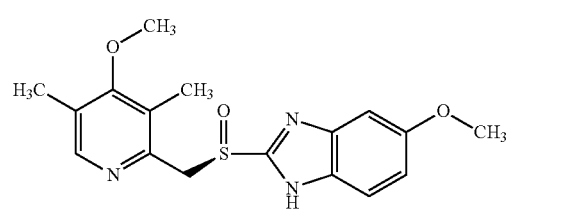

III(f)

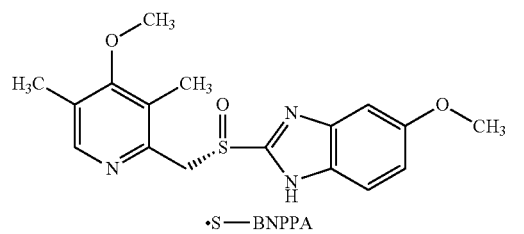

III(g)

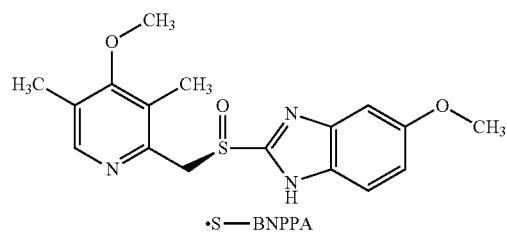

III(h)

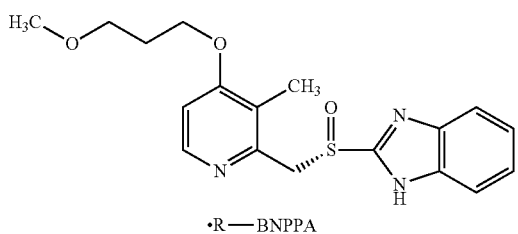

III(i)

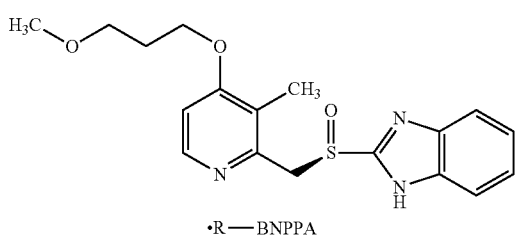

III(j)

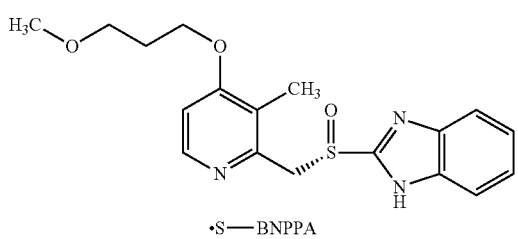

III(k)

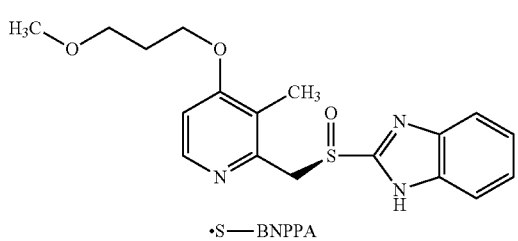

III(l)

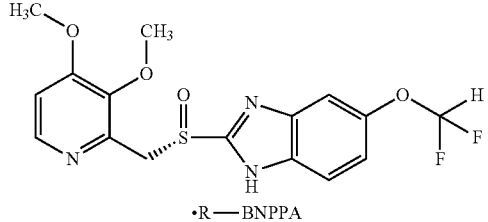

III(m)

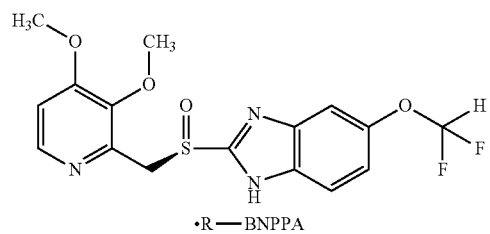

III(n)

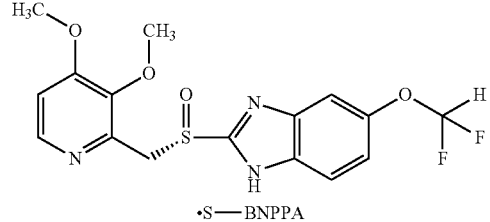

III(o)

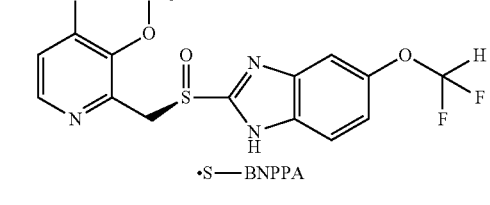

III(p)

The invention will now be further described by the following examples, which are illustrative rather than limiting

EXAMPLES

Example 1

Preparation of R-2-[[[3-methyl-4-(2,2,2-trifluoro-ethoxy)-2-pyridinyl]methyl]sulfinyl]-1H-benzimidazole.R-1,1'-binaphthyl-2-2'-diyl hydrogen phosphate (R-lansoprazole-(R)-BNPPA complex)

R-1,1'-binaphthyl-2-2'-diyl hydrogen phosphate (31.25 gm, 0.0897 moles) was added to a solution of 2-[[[3-methyl-4-(2,2,2-trifluoro-ethoxy)-2-pyridinyl]methyl]sulfinyl]-1H-benzimidazole (25 gm, 0.0677 moles) and powder sodium hydroxide (7.5 gm) in a mixture of ethyl acetate and cyclohexane (625 ml, 1:1.5) at room temperature. The reaction mixture was heated to 50 to 55° C. for 30 minutes and then the solution was cooled to 40° C. The solid obtained was collected by filtration, washed twice with a mixture of ethyl acetate and cyclohexane (100 ml, 1:1), and then dried at 45 to 50° C. under vacuum for 4 hours to obtain 29 gm of R-lansoprazole-(R)-BNPPA complex (chiral purity: 70%).

Example 2

Preparation of R-lansoprazole-(R)-BNPPA complex

R-1,1'-binaphthyl-2-2'-diyl hydrogen phosphate (12.5 gm, 0.0359 moles) was added to a solution of 2-[[[3-methyl-4-(2,2,2-trifluoro-ethoxy)-2-pyridinyl]methyl]sulfinyl]-1H-benzimidazole (10 gm, 0.0271 moles) and powder sodium hydroxide (3 gm) in a mixture of toluene and cyclohexane (250 ml, 1:1.5) at room temperature and heated to 50 to 55° C. for 30 minutes. Then the solution was cooled to 40° C., filtered. The solid obtained was washed twice with a mixture of toluene and cyclohexane (40 ml, 1:1), and then dried at 45 to 50° C. under vacuum for 4 hours to obtain 12 gm of R-lansoprazole-(R)-BNPPA complex (chiral purity: 78%).

R-lansoprazole-(R)-BNPPA complex obtained above was stirred in a mixture of benzene and cyclohexane and filtered to get the pure R-lansoprazole-(R)-BNPPA complex (chiral purity: 99%).

Example 3

Preparation of R-lansoprazole-(R)-BNPPA complex

R-1,1'-binaphthyl-2-2'-diyl hydrogen phosphate (17.6 gm, 0.05 moles) was added to a solution of 2-[[[3-methyl-4-(2,2,2-trifluoro-ethoxy)-2-pyridinyl]methyl]sulfinyl]-1H-benzimidazole (25 gm, 0.0677 moles) and powder sodium hydroxide (7.5 gm) in a mixture of benzene and cyclohexane (625 ml, 1:1.5) at room temperature. The reaction mixture was heated to 50 to 55° C. for 30 minutes and then the solution was cooled to 40° C. The solid obtained was collected by filtration, washed twice with a mixture of benzene and cyclohexane (100 ml, 1:1), and then dried at 45 to 50° C. under vacuum for 4 hours to obtain 28 gm of R-lansoprazole-(R)-BNPPA complex (chiral purity: 82%).

Example 4

Preparation of R-lansoprazole-(R)-BNPPA complex

R-1,1'-binaphthyl-2-2'-diyl hydrogen phosphate (51.86 gm, 0.149 moles) was added to a solution of 2-[[[3-methyl-4-(2,2,2-trifluoro-ethoxy)-2-pyridinyl]methyl]sulfinyl]-1H-benzimidazole (50 gm, 0.135 moles) and powder sodium hydroxide (15 gm) in a mixture of benzene and cyclohexane (1250 ml, 1:1.5) at room temperature. The reaction mixture was heated to 50 to 55° C. for 30 minutes and then the solution was cooled to 40° C. The separated solid was filtered, washed twice with a mixture of benzene and cyclohexane (200 ml, 1:1), and then dried at 45 to 50° C. under vacuum for 4 hours to obtain 55 gm of R-lansoprazole-(R)-BNPPA (chiral purity: 95.5%).

Example 5

Preparation of R-lansoprazole-(R)-BNPPA complex

R-1,1'-binaphthyl-2-2'-diyl hydrogen phosphate (12.5 gm, 0.0359 moles) was added to a solution of 2-[[[3-methyl-4-(2,2,2-trifluoro-ethoxy)-2-pyridinyl]methyl]sulfinyl]-1H-benzimidazole (10 gm, 0.0271 moles) and powder sodium hydroxide (3 gm) in a mixture of benzene and cyclohexane (250 ml, 1:1.5) at room temperature and heated to 50 to 55° C. for 30 minutes. Then the solution was cooled to 40 deg C., filtered. The solid obtained was washed twice with a mixture of benzene and cyclohexane (40 ml, 1:1), and then dried at 45 to 50 deg C. under vacuum for 4 hours to obtain 10 gm of R-lansoprazole-(R)-BNPPA (chiral purity: 99.8%).

Example 6

Preparation of R-lansoprazole (Dexlansoprazole)

To a stirred solution of R-lansoprazole-(R)-BNPPA complex (10 gm) in ethyl acetate (200 ml) was slowly added sodium bicarbonate (30 ml, 10%) at 5 to 10° C. The solution was stirred for 30 minutes at 5 to 10° C. and layers were separated. The organic layer was washed with water and concentrated on a rotavapor. The residue obtained was dissolved in methanol (10 ml) and was added to ice cold water (100 ml) dropwise, stirred for 30 minutes. The solid obtained was collected by filtration and the solid was dried at 45 to 50° C. under vacuum for 12 hours to obtain 3 gm of dexlansoprazole (chiral purity: 99.96%).

Example 7

Preparation of S-lansoprazole-(S)-BNPPA complex

S-1,1'-binaphthyl-2-2'-diyl hydrogen phosphate (12.5 gm, 0.0359 moles) was added to a solution of 2-[[[3-methyl-4-(2,2,2-trifluoro-ethoxy)-2-pyridinyl]methyl]sulfinyl]-1H-benzimidazole (10 gm, 0.0271 moles) and powder sodium hydroxide (3 gm) in a mixture of toluene and cyclohexane (250 ml, 1:1.5) at room temperature and heated to 50 to 55° C. for 30 minutes. Then the solution was cooled to 40° C., filtered. The solid obtained was washed twice with a mixture of toluene and cyclohexane (40 ml, 1:1), and then dried at 45 to 50° C. under vacuum for 4 hours to obtain 11.5 gm of S-lansoprazole-(S)-BNPPA complex (chiral purity: 88%).

Example 8

Preparation of S-lansoprazole-(S)-BNPPA complex

S-1,1'-binaphthyl-2-2'-diyl hydrogen phosphate (31.25 gm, 0.0899 moles) was added to a solution of 2-[[[3-methyl-4-(2,2,2-trifluoro-ethoxy)-2-pyridinyl]methyl]sulfinyl]-1H-benzimidazole (25 gm, 0.0677 moles) and powder sodium hydroxide (7.5 gm) in a mixture of benzene and cyclohexane (250 ml, 1:1.5) at room temperature. The reaction mixture was heated to 50 to 55° C. for 30 minutes and then the solution was cooled to 40° C. The separated solid was filtered, washed twice with a mixture of benzene and cyclohexane (100 ml, 1:1), and then dried at 45 to 50° C. under vacuum for 4 hours to obtain 23.5 gm of S-lansoprazole-(S)-BNPPA complex (chiral purity: 98.8%).

Example 9

Preparation of S-lansoprazole

To a stirred solution of S-lansoprazole-(S)-BNPPA complex (23.5 gm) in ethyl acetate (450 ml) was slowly added sodium bicarbonate (72 ml, 10%) at 5 to 10° C. The solution was stirred for 30 minutes at 5 to 10° C. and layers were separated. The organic layer was washed with water and concentrated on a rotavapor. The residue obtained was dissolved in methanol (25 ml) and was added to ice cold water (250 ml) dropwise, stirred for 30 minutes. The solid obtained was collected by filtration and the solid was dried at 45 to 50° C. under vacuum for 12 hours to obtain 3 gm of S-lansoprazole (chiral purity: 99.96%).

Example 10

Preparation of 5-methoxy-2-[(S)-[(4-methoxy-3,5-dimethyl-2-pyridinyl)methyl]sulfinyl]-1H-benzimidazole.R-1,1'-binaphthyl-2-2'-diyl hydrogen phosphate (S-omeprazole-(R)-BNPPA complex)

R-1,1'-binaphthyl-2-2'-diyl hydrogen phosphate (12.5 gm, 0.0359 moles) was added to a solution of 5-methoxy-2-[[(4-methoxy-3,5-dimethyl-2-pyridinyl)methyl]sulfinyl]-1H-benzimidazole (10 gm, 0.0289 moles) and powder sodium hydroxide (3 gm) in a mixture of benzene and cyclohexane (250 ml, 1:1.5) at room temperature and heated to 50 to 55° C. for 30 minutes. Then the solution was cooled to 40° C., filtered. The solid obtained was washed with a mixture of benzene and cyclohexane (40 ml, 1:1), and then dried at 45 to 50 deg C. under vacuum for 4 hours to obtain 5 gm of S-omeprazole-(R)-BNPPA complex (chiral purity: 75%).

Example 11

Preparation of S-omeprazole-(R)-BNPPA complex

R-1,1'-binaphthyl-2-2'-diyl hydrogen phosphate (7.5 gm, 0.0215 moles) was added to a solution of 5-methoxy-2-[[(4-methoxy-3,5-dimethyl-2-pyridinyl)methyl]sulfinyl]-1H-benzimidazole (5 gm, 0.0144 moles) and powder sodium hydroxide (1 gm) in a mixture of benzene and cyclohexane (250 ml, 1:1.5) at room temperature and heated to 50 to 55° C. for 30 minutes. Then the solution was cooled to 40° C., filtered. The solid obtained was washed with a mixture of benzene and cyclohexane (40 ml, 1:1), and then dried at 45 to 50° C. under vacuum for 4 hours to obtain 3 gm of S-omeprazole-(R)-BNPPA complex (chiral purity: 78%).

Example 12

Preparation of S-omeprazole-(R)-BNPPA complex

R-1,1'-binaphthyl-2-2'-diyl hydrogen phosphate (6 gm, 0.017 moles) was added to a solution of 5-methoxy-2-[[(4-methoxy-3,5-dimethyl-2-pyridinyl)methyl]sulfinyl]-1H-benzimidazole (10 gm, 0.0289 moles) and ethanol (350 ml) at room temperature and stirred for 30 minutes at room temperature. The solid obtained was collected by filtration, washed with ethanol, and then dried at 40 to 45° C. under vacuum for 4 hours to obtain 9 gm of S-omeprazole-(R)-BNPPA complex (chiral purity: 83.5%).

Example 13

Preparation of S-omeprazole (Esomeprazole)

To a stirred solution of S-omeprazole-(R)-BNPPA complex (10 gm) in ethyl acetate (200 ml) was slowly added sodium bicarbonate (30 ml, 10%) at 5 to 10° C. The solution was stirred for 30 minutes at 5 to 10° C. and layers were separated. The organic layer was washed with water and concentrated on a rotavapor. The residue obtained was dissolved in methanol (10 ml) and was added to ice cold water (50 ml) dropwise, stirred for 30 minutes. The solid obtained was collected by filtration and the solid was dried at 45 to 50° C. deg C under vacuum for 12 hours to obtain 3 gm of esomeprazole (chiral purity: 84%).

Example 14

Preparation of S-pantoprazole-(R)-BNPPA complex

R-1,1'-binaphthyl-2-2'-diyl hydrogen phosphate (11 gm, 0.031 moles) was added to a solution of 5-(difluoromethoxy)-2-[[(3,4-dimethoxy-2-pyridinyl)methyl]sufinyl]-1H-benzimidazole (pantoprazole) (10 gm, 0.026 moles) and powder sodium hydroxide (3 gm) in a mixture of benzene and cyclohexane (250 ml, 1:1.5) at room temperature and heated to 50 to 55° C. for 30 minutes. Then the solution was cooled to 40° C., filtered. The solid obtained was washed with a mixture of benzene and cyclohexane (40 ml, 1:1), and then dried at 45 to 50 deg C. under vacuum for 4 hours to obtain 4.5 gm of S-pantoprazole-(R)-BNPPA complex (chiral purity: 98%).

Example 15

Preparation of S-rabeprazole-(R)-BNPPA complex

R-1,1'-binaphthyl-2-2'-diyl hydrogen phosphate (12 gm, 0.034 moles) was added to a solution of 2-[[[4-(3-methoxypropoxy)-3-methyl-2-pyridinyl]methyl]sulfinyl]-1H-benzimidazole (rabeprazole) (10 gm, 0.028 moles) and powder sodium hydroxide (3 gm) in a mixture of benzene and cyclohexane (250 ml, 1:1.5) at room temperature and heated to 50 to 55° C. for 30 minutes. Then the solution was cooled to 40° C., filtered. The solid obtained was washed with a mixture of benzene and cyclohexane (40 ml, 1:1), and then dried at 45 to 50 deg C. under vacuum for 4 hours to obtain 4.7 gm of S-rabeprazole-(R)-BNPPA complex (chiral purity: 98.2%).

Example 16

Preparation of S-pantoprazole

Example 6 was repeated using S-pantoprazole-(R)-BNPPA complex obtained as in example 15 instead of R-lansoprazole-(R)-BNPPA complex to obtain S-pantoprazole.

Example 17

Preparation of S-rabeprazole

Example 6 was repeated using S-rabeprazole-(R)-BNPPA complex obtained as in example 16 instead of R-lansoprazole-(R)-BNPPA complex to obtain S-rabeprazole.

We claim:

1. A process for resolution of substituted 2-(2-pyridinylmethylsulphinyl)-1H-benzimidazoles of formula (I) or a mixture thereof;

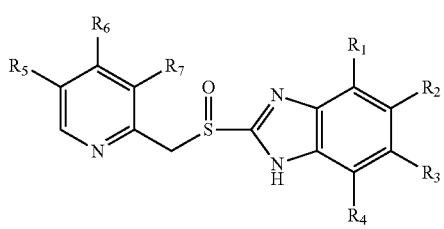

I

Wherein $R_1$-$R_4$ are the same or different and selected from hydrogen, alkyl, alkoxy, halogen, halo-alkoxy, alkylcarbonyl, alkoxycarbonyl, oxazolyl, trifluoroalkyl, or adjacent groups $R_1$-$R_4$ form ring structures which may be further substituted; and $R_5$, $R_6$ and $R_7$ are same or different and selected from hydrogen, alkyl, alkylthio, alkoxy optionally substituted by fluorine, alkoxyalkoxy, dialkylamino, piperidino, morpholino, halogen, phenylalkyl and phenylalkoxy; which comprises:

a) reacting substituted 2-(2-pyridinylmethylsulphinyl)-1H-benzimidazoles of formula (I) or a mixtures thereof with a chiral 1,1'-binaphthyl-2-2'-diyl hydrogen phosphate (BNPPA) to obtain corresponding diastereomer complexes;

b) isolating preferentially one diastereomer complex from the mixture of diastereomer complexes; and c) converting the isolated diastereomer complex to the corresponding enantiomer of the compound of formula (I).

2. The process according to claim 1, wherein $R_5$ and $R_7$ are methyl; $R_2$ and $R_6$ are methoxy; and $R_1$, $R_3$, and $R_4$ are hydrogen.

3. The process according to claim 1, wherein $R_1$, $R_2$, $R_3$, $R_4$, and $R_5$ are hydrogen; $R_7$ is methyl; and $R_6$ may be —O(CH$_2$)$_3$OCH$_3$.

4. The process according to claim 1, wherein $R_1$, $R_2$, $R_3$, $R_4$ and $R_5$ is hydrogen; $R_7$ is methyl; and $R_6$ may —OCH$_2$CF$_3$.

5. The process according to claim 1, wherein $R_1$, $R_3$, $R_4$, and $R_5$ are hydrogen; $R_2$ is difluoromethoxy; and $R_6$ and $R_7$ are methoxy.

6. The process according to claim 1, wherein the reaction in step (a) process is carried out in solvent or a mixture thereof, further wherein the process of step (a) comprises adding a base.

7. The process according to claim 6, wherein the solvent used in the process is selected from the group consisting of alcohols, methanol, ethanol, isopropyl alcohol, alkyl benzene, toluene, xylene, cyclohexane, hexane, ethyl acetate, benzene, and a mixture thereof.

8. The process according to claim 7, wherein the solvent used in the process is selected from a mixture of benzene or toluene or ethyl acetate and cyclohexane.

9. The process according to claim 8, wherein the solvent used in the process is a mixture of benzene and cyclohexane.

10. The process according to claim 6, wherein the base is selected from the group consisting of inorganic bases, alkaline metal hydroxides, alkaline metal carbonates, alkaline metal bicarbonates, ammonia, organic bases, trimethylamine, and triethylamine.

11. The process according to claim 1, wherein the reaction in step (b) crystallization is carried out in a solvent.

12. The process according to claim 11, wherein the solvent is selected from the group consisting of alkyl benzene, toluene, xylene, benzene, cyclohexane, esters, ethyl acetate, methyl acetate, isopropyl acetate, tert-butyl methyl acetate, ethyl formate, alcohols, methanol, ethanol, and a mixture thereof.

13. The process according to claim 12, wherein the solvent is selected from a mixture of toluene, ethyl acetate, benzene and cycloheaxne.

14. The process according to claim 1, wherein the reaction in step (c) conversion is carried out in water or solvent; or a mixture thereof, further wherein the process of step (c) comprises adding a base.

15. The process according to claim 14, wherein the solvent is selected from the group consisting of an alcohol, methanol, ethanol, isopropyl alcohol, ketones, acetone, methyl ethyl ketone, methyl isopropyl ketone, methyl t-butyl ketone, acetonitrile, ethyl acetate, isopropyl acetate, methyl acetate, N,N-dimethylformamide, tetrahydrofuran, and a mixture thereof.

16. The process according to claim 15, wherein the solvent is selected from methanol, ethanol, isopropyl alcohol and ethyl acetate.

17. The process according to claim 16, wherein the solvent is a mixture of water and ethyl acetate.

18. The process according to claim 14, wherein the base is selected from the group consisting of inorganic bases, alkaline metal hydroxides, alkaline metal carbonates, alkaline metal bicarbonates, ammonia, organic bases, trimethylamine, and triethylamine.

19. A compound selected from the formula II(i) to II(iv) or a mixture thereof:

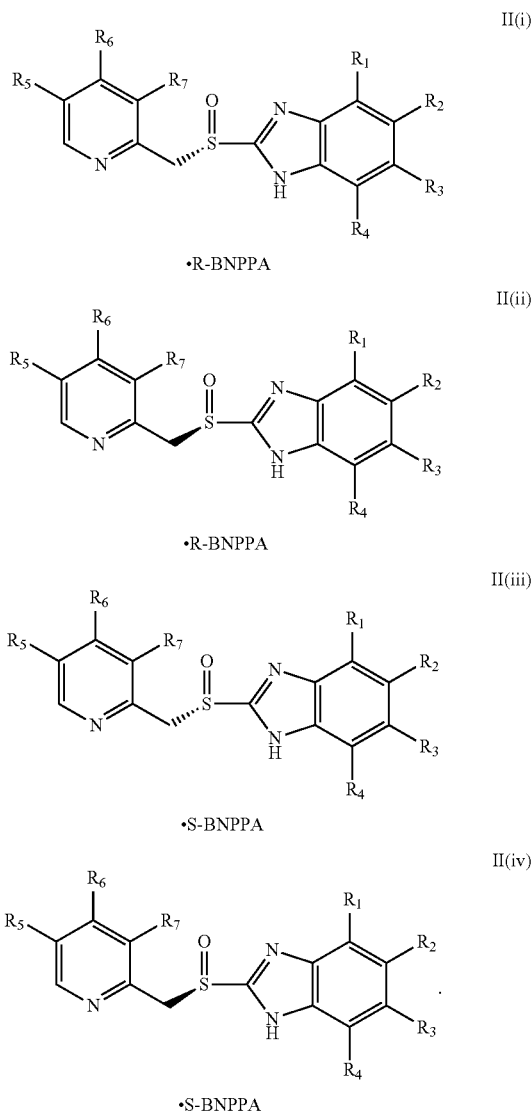

20. The compound according to claim 19, which is compound of formula III(a) to III(p):

III(a) · R—BNPPA

III(b) · R—BNPPA

III(c) · S—BNPPA

III(d) · S—BNPPA

III(e) · R—BNPPA

III(f) · R—BNPPA

III(g) · S—BNPPA

III(h) · S—BNPPA

III(i) · R—BNPPA

III(j) · R—BNPPA

III(k) · S—BNPPA

III(l) · S—BNPPA

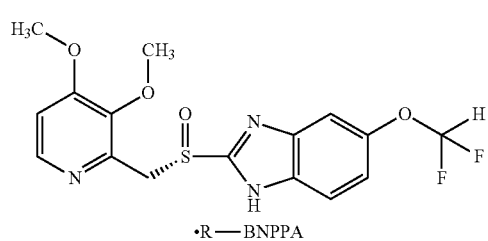
III(m)
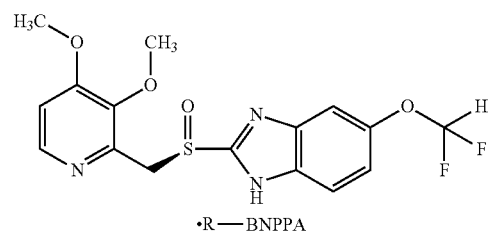
III(n)
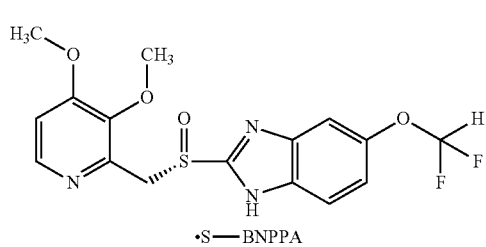
III(o)
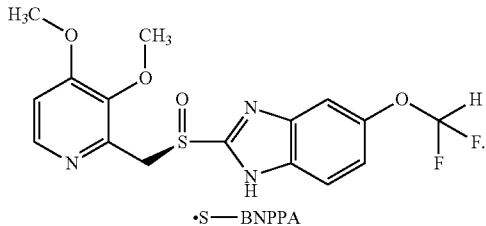
III(p)
* * * * *